(12) United States Patent
Dotto

(10) Patent No.: US 7,202,392 B2
(45) Date of Patent: Apr. 10, 2007

(54) IN VIVO SCREENING ARRAY

(75) Inventor: G. Paolo Dotto, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 38 days.

(21) Appl. No.: 10/470,818

(22) PCT Filed: Jan. 16, 2002

(86) PCT No.: PCT/US02/01387

§ 371 (c)(1),
(2), (4) Date: Jan. 7, 2004

(87) PCT Pub. No.: WO02/061116

PCT Pub. Date: Aug. 8, 2002

(65) Prior Publication Data

US 2004/0106152 A1    Jun. 3, 2004

Related U.S. Application Data

(60) Provisional application No. 60/265,230, filed on Jan. 13, 2001.

(51) Int. Cl.
*A01K 67/00* (2006.01)
*G01N 33/00* (2006.01)

(52) U.S. Cl. .................. 800/3; 800/8; 800/18
(58) Field of Classification Search .......... 800/3, 800/13, 18, 25, 8
See application file for complete search history.

(56) References Cited

U.S. PATENT DOCUMENTS

| 4,914,022 | A | | 4/1990 | Furmanski et al. ............ 435/7 |
| 5,648,061 | A | | 7/1997 | Bernstein et al. ............ 424/9.2 |
| 5,735,288 | A | * | 4/1998 | Fishman .................... 600/556 |
| 5,753,439 | A | | 5/1998 | Smith et al. ................ 435/6 |
| 6,083,763 | A | | 7/2000 | Balch ........................ 436/518 |
| 6,118,044 | A | | 9/2000 | Karasuyama et al. .......... 800/3 |
| 6,183,995 | B1 | | 2/2001 | Burmer et al. ............. 435/91.1 |

FOREIGN PATENT DOCUMENTS

WO    WO 99/30743    6/1999

OTHER PUBLICATIONS

Kappel et al. Current Biology, 1992, 3: 548-553.*
Mullins et al. Hypertension, 1993, 22: 630-633.*
Houdebine et al. Journal of Biotechnology, 1994, 34: 269-287.*
Wall R.J. Theriogenology, 1996, 45: 57-68.*
Mullins et al. Journal of Clinical Investigation, 1996, 98(11): S37-S40.*
Cameron E. Molecular Biology, 1997, 7: 253-265.*
Sigmund C. Arterioscler. Thromb. Vasc. Biol., 2000, 20: 1425-1429.*
Niemann H. Transgenic Research, 1998, 7: 73-75.*
"Induced Mutant Resource (IMR) Transgenic and Targeted Mutant Mice," The Jackson Laboratory, http://web.archive.org/web/20000901042229/www.jax.org/resources . . . downloaded Dec. 22, 2005.
Markkula, et al., "Transgenic Animals and Gonadotrophins," *Reviews of Reproduction* 1: 97-106 (1996).
Missero et al., "Skin-specific Expression of a Truncated Ela Oncoprotein Binding to p105-Rb Leads to Abnormal Hair Follicle Maturation Without Increased Epidermal Proliferation," *J. Cell Bio.* 121(5):1109-20, Jun. 1993.
Wolf et al., "Use of Transgenic Animals in Understanding Molecular Mechanisms of Toxicity", *J. Pharm. Pharmacol.* 50: 567-74 (1998).

* cited by examiner

*Primary Examiner*—Michael C. Wilson
(74) *Attorney, Agent, or Firm*—Fish & Richardson P.C.

(57) ABSTRACT

The invention features methods of evaluating the effect of a plurality of different treatments or compounds on a tissue. The method includes providing a tissue from an animal; contacting the tissue with a plurality of treatment, forming on the tissue an array of a plurality of regions or addresses. The method includes the use of a two dimensional array member to contact the plurality of treatments with the tissue and/or to evaluate their effect. The methods are useful for screening large numbers of therapeutic or cosmetic compounds.

15 Claims, No Drawings

IN VIVO SCREENING ARRAY

CROSS-REFERENCE TO RELATED APPLICATIONS

This application claims priority to U.S. application Ser. No. 60/265,230, filed on Jan. 31, 2001, the content of which are hereby incorporated by reference.

BACKGROUND

Animal models are widely used as screening tools for evaluating compounds or treatments during drug or cosmetic development. The available in vitro methods for screening compounds principally involve the use of cell monolayers, co-cultures or isolated skin explants. In vivo methods include the mouse ear swelling test (Gad et al. (1986). Toxicol Appl Pharmacol 84:93–114; Descotes (1988) J Toxicol-Cutan Ocular Toxicol 7:263–272), and the murine local lymph node assay (LLNA) (Kimber et al. (1989) Contact Dermat 21:215–220; Dearman et al. (1999) J Appl Toxicol 19(5):299–306). Transgenic mice models have also been used as screening tools for testing the effect of compounds applied to the skin on the expression of a transgene (Berstein et al., U.S. Pat. No. 5,648,061; Burgeson et al., PCT International Publication No. WO 99/30743). These models require the use of multiple animals and multiple experiments for thorough assessment and controls in screening assays.

SUMMARY

The invention provides methods and devices which minimize the effort, and in some embodiments, the number of live animals, needed to evaluate a large number of compounds or treatments, e.g., toxins, drugs, cosmetics, or light or radiation treatments. The methods are useful for screening, e.g., toxins, allergens, or potential therapeutic or cosmetic compounds or treatments, for their effect on the tissue, e.g., a group of cells, a tissue or organ explant, or an in vivo tissue or organ, e.g., skin, of a subject, e.g., an animal, e.g., an experimental rodent, e.g., a mouse or a transgenic mouse.

In one aspect, the invention features, a method of evaluating the effect of a plurality of different treatments, e.g., the delivery of a plurality of different compounds; a compound at a plurality of different concentrations or dosages; a plurality of different dosages or wavelengths of light; or a plurality of different types or dosages of radiation. The method includes: providing a tissue from an animal; contacting the tissue with a plurality of treatments, forming on the tissue an array of a plurality of individually addressable regions or addresses, each region or address of the plurality being provided with a test treatment which differs from those at other addresses of the plurality; and evaluating a parameter related to the treatment at each of the plurality of regions or addresses. The method includes the use of a two dimensional array member to contact the plurality of treatments with the tissue to form the array and/or to evaluate the effect of the treatments. Contacting the tissue with the treatments can be performed by, e.g., applying a compound to the surface of the tissue; injecting a compound into the tissue; or directing a beam of light or radiation onto the tissue. The parameter measured can be evaluated by the appearance or morphology of the tissue, e.g., contact allergy, contact dermatitis, redness, thickness, swelling, hyperemia, pruritis, papules, vesicles, bullae, erythema, flaking, or edema. The effect can be evaluated ex vivo, e.g., on a tissue or organ explant, e.g., a skin explant; or in vivo, e.g., on the tissue of a live animal, e.g. skin.

In a preferred embodiment, the array includes at least 4 addresses, more preferably 8, 16, 32, 64, or 128 addresses.

In a preferred embodiment, the addresses are present at a density of at least one address/cm$^2$, more preferably 4, 10, 20, 40, 50, or 100, or more addresses/cm$^2$.

In a preferred embodiment, the tissue is skin.

In a preferred embodiment, the parameter to be evaluated is redness, thickness, swelling, edema, or flaking.

In one aspect, the invention features, a method of evaluating the effect of a plurality of different treatments, e.g., the delivery of a plurality of different compounds; a compound at a plurality of different concentrations or dosages; a plurality of different dosages or wavelengths of light; or a plurality of different types or dosages of radiation. The effect can be the effect on the level of one or more gene products, e.g., the effect on the expression of one or more genes. The method includes: (1) providing a transgenic animal, e.g., a mouse, having a transgene which includes a nucleic acid which encodes a reporter molecule functionally linked to the control region of a first gene (optionally the animal can include a second transgene having a second control sequences linked to the same or a different reporter molecule sequence); (2) contacting a tissue from the transgenic animal (in vivo or ex vivo) with a plurality of different treatments, e.g., a plurality of different test compounds, a plurality of different concentrations or dosages of a compound, or a plurality of different types or dosages of light or radiation, forming on the tissue an array of a plurality of individually addressable regions or addresses, each region or address of the plurality including a test treatment (or combination of test treatments) which differs, e.g. by structure, concentration, or dosage, from those at other addresses of the plurality; (3) evaluating a signal produced by the reporter molecule at each of the plurality of regions or addresses, the presence or strength of which is correlated with the expression of the first gene; and where a two dimensional array member is used to contact the compounds with the tissue to form the array and/or to evaluate the signal. The signal can be, e.g., conductivity, temperature, color, or the production of light. Fluorescence is the most preferred signal.

In a preferred embodiment the signals are evaluated by scanning the tissue, e.g., skin, or a portion of an organ, for the presence of light of a predetermined wavelength.

In a preferred embodiment, the signal is generated by proximity methods, e.g., assays where one member of a signal generating pair is a signal generator, and the other is a quencher, or where one member of a signal generating pair excites the other.

In a preferred embodiment the array includes at least 4 addresses more preferably 8, 16, 32, 64, or 128 addresses.

In a preferred embodiment the addresses are present at a density of at least one adress/cm$^2$, more preferably 4, 10, 20, 40, 50, or 100, or more addresses/cm$^2$.

In another aspect, the invention features, a method of evaluating the effect of a plurality of different treatments, e.g., the delivery of a plurality of different compounds; the provision of a compound at a plurality of different concentrations; a plurality of different dosages or wavelengths of light; or a plurality of different types or dosages of radiation, on a tissue or other population of cells. The method includes: (1) providing a tissue (or other population of cells) having a reporter agent which produces a signal, e.g., light, e.g., fluorescence, which is correlated with a biological state, e.g., a signal which is indicative of one or more of, the migration of a molecule, e.g., a labeled molecule into or out of an address or region; the binding of a first molecule to a second molecule; the concentration of an analyte, the expression of a gene; or of a biological state, e.g., a developmental stage, a disease or non-disease state, e.g., inflammation; (2) contacting the tissue, e.g., tissue from a transgenic animal (in vivo or ex vivo) with a plurality of different treatments, or a plurality of different concentrations or dosages of a treatment, forming on the tissue an array of a plurality of individually addressable regions or addresses, each region or address of the plurality including a test treatment which differs, e.g. by structure, dosage, or concentration, from those at other addresses of the plurality; and (3) evaluating a signal produced by the reporter agent (e.g., the production of light, e.g., fluorescence) at each of the plurality of regions or addresses; where, optionally, the contacting of the compounds with the tissue to form the array, and/or the evaluation of signal, is performed with a two dimensional array member which is contacted with the tissue.

In a preferred embodiment the signals are evaluated by scanning the tissue, e.g., skin, or a portion of an organ, for the presence of light of a predetermined wavelength.

In a preferred embodiment the array includes at least four addresses.

In a preferred embodiment the addresses are present at a density of at least one adress/cm$^2$.

In another aspect, the invention features an array which includes an animal tissue, e.g., mouse skin, which has on it a plurality of addresses, e.g., a grid, where at least two addresses on the tissue are contacted with a treatment or compound.

In a preferred embodiment, the tissue is skin.

In a preferred embodiment, the array includes at least 4 addresses.

In a preferred embodiment, the addresses are present at a density of at least one adress/cm$^2$.

In a preferred embodiment, at least two addresses on the tissue are injected with a compound.

In another aspect, the invention provides an array described herein, e.g., an array formed on an animal.

The details of one or more embodiments of the invention are set forth in the accompanying drawings and the description below. Other features, objects, and advantages of the invention will be apparent from the description and drawings, and from the claims.

DETAILED DESCRIPTION

The methods described herein provides a rapid, quantitative method to measure the effect of a plurality of treatments on a tissue, while minimizing the number of animals used in an assay. A plurality of treatments encompasses, e.g., a plurality of physical treatments or different dosages or types of physical treatments, e.g., exposure to light, heat, or radioactivity; delivery of a plurality of different compounds; delivery of combinations of compounds; or delivery of different concentrations, formulations, or dosages, of the same or a combination of compounds.

The tissue used in the methods described herein can be, e.g., a cell, tissue or organ explant, or a group of cells, a tissue, or organ in vivo. The subject is preferably an animal, e.g., an experimental rodent. The subject can be a transgenic or a non-transgenic animal, e.g., a mouse. Preferably, the tissue is skin. The methods allow for the in situ evaluation of a plurality of treatments or compounds in vivo, e.g., the evaluation of the effect of a plurality of compounds on the skin of a mouse, e.g., the skin of a mouse ear. Treatments or compounds which can be tested include, but are not limited to, environmental contaminants, toxic compounds, cosmetic compounds, therapeutic compounds, radiation, or light exposure. The methods can be used to screen the treatments or compounds, e.g., for allergic response, toxicity, carcinogenicity, or therapeutic or cosmetic efficacy.

The treatments or compounds are contacted with the cells, tissue, or organ, and/or are evaluated, by means of a two dimensional member which forms on the cells, tissue, or organ, an array, e.g., a grid, of a plurality of individually addressable regions of tissue or cells, each of which can be exposed to a treatment or a compound. For example, the two-dimensional member can form a grid on a portion of the skin of an animal, e.g., a hairless mouse. The two-dimensional member can form at least 4, preferably 8, more preferably 15, 20, 30, 40, 50, 100, or more, individually addressable regions on the tissue. The density of the addresses or regions can be at least one address or region per cm$^2$, preferably 4, 8, 16, 32, 64, 128, or more, addresses or regions per cm$^2$.

A treatment or compound can be contacted with the tissue by, e.g., contacting a compound with the surface of the tissue at an address of the array e.g., by applying the compound epidermally to the surface of the skin; injecting a compound into one or more cells of a tissue within an address of the array, e.g., intradermally; or directing a beam of light or radiation onto one or more cells of a tissue within an address of the array.

The effect of a treatment or compound on a tissue can be an effect which can be evaluated by the appearance or morphology of the tissue, e.g., skin. For example, the arrays can be used to assess the presence or absence of contact allergy, contact dermatitis, skin swelling, hyperemia, pruritis, papules, vesicles, bullae, erythema, flaking, or edema. Such evaluation can be performed, e.g., through appropriate instrumentation, e.g., through a microscope.

In some embodiments, the invention includes a transgenic animal containing a transgene which includes a nucleic acid which encodes a reporter molecule functionally linked to the control region, e.g., a promoter or enhancer, of a gene of interest. The transgenic animal can include a second transgene having a control sequence of a second gene of interest linked to the same or a different reporter molecule sequence. The array member can be used to evaluate the effect of a plurality of compounds or treatments on the expression of the gene or genes of interest by evaluating the activity of the reporter gene at each of the addresses of the array.

Preferred genes of interest include those whose expression is indicative or predictive of a specific biological response, e.g., genes involved in sensitization, toxic response, allergic response, hyperproliferation, or pigmentation. For example, although clinical manifestations of delayed contact hypersensitivity (such as erythema or edema) may not be apparent for days after the application of a contact allergen to the skin, interleukin (IL)-1β mRNA signals increase within as early as 15 minutes after contact with a sensitizing hapten (Enk & Katz (1992) *Proc Natl Acad Sci USA* 89:1398–1402), followed by an increase in TNF-α mRNA within the epidermis (Enk et al. (1993)*J Immunol* 150: 3698–3704). Hapten application also induces the expression of epidermal adhesion molecules such as ICAM-1, E-selectin, and vascular adhesion molecule (VCAM)-1 (Silber et al. (1994) *J Clinical Invest* 93:1554–1563; Goebeler et al (1993) *J Investig Dermatol* 100: 759–765). Thus, a transgenic animal described herein can include a reporter gene functionally linked to a control region of, e.g., an epidermal cytokine, e.g., interleukin, interferon, TNF, TGF, GM-CSF, or G-CSF; or an epidermal cell adhesion molecule, e.g., ICAM, E-selectin, or VCAM.

Other preferred genes of interest include genes involved in signal transduction, cell-cell interaction or communication, disease progression, or cell differentiation and proliferation, e.g., epithelial cell differentiation and proliferation, e.g., EGF. Other genes of interest can be identified by a skilled practitioner depending in the nature of the compound or treatment being assayed.

Reporter Genes

In some embodiments which include a transgenic animal, a reporter gene can be functionally linked to the control region of a gene of interest. In a preferred embodiment, the reporter gene encodes a polypeptide product detectable by an intrinsic activity associated with that product, and which is not otherwise produced by the host cell. For instance, the reporter gene may encode a gene product that, by enzymatic activity, gives rise to a detection signal based on color, fluorescence, or luminescence. Examples of reporter molecules which are enzymes detectable by a color signal include fluorescent proteins, e.g., green fluorescent protein (GFP), or blue fluorescent protein; luciferase; chloramphenicol acetyl transferase (CAT); β-galactosidase; β-lactamase; or secreted placental alkaline phosphatase. Other reporter molecules and other enzymes whose function can be detected by appropriate chromogenic or fluorogenic substrates are known to those skilled in the art.

A preferred signal is fluorescence. Preferably, the signal is a quantitative or semi-quantitative function of transcriptional activation of the gene of interest to which the reporter gene is coupled. A preferred reporter molecule is GFP, which allows for direct, in vivo detection of fluorescence (reviewed in Tsien (1998) *Annu Rev Biochem* 67:509–44).

The transgenic animal can be used to provide a tissue, ex-vivo or in vivo, for use in the screening array disclosed herein. The detection signal produced by the reporter molecule at each of the plurality of addressees in the array, e.g., on the skin of the transgenic animal, can be evaluated by a two-dimensional array member. For example, the signals can be evaluated by scanning the tissue, e.g., skin, or a portion of an organ, for the presence of color, or light of a predetermined wavelength.

Proximity Methods

In some embodiments, the signal is generated using proximity methods. Proximity methods include those methods whereby a signal is modulated, e.g., generated, when a first member and second member of a proximity detection pair are brought into close proximity.

A proximity detection pair will usually have two members, the first member, e.g., an energy absorbing donor or a photosensitive molecule and the second member, e.g., an energy absorbing acceptor or a chemiluminescer particle. When the first and second members of the proximity detection pair are brought into close proximity, a signal is generated.

Examples of proximity methods include the following:

Fluorescence Resonance Energy Transfer (FRET)

Fluorescence resonance energy transfer (FRET) is based on a donor fluorophore that absorbs a photon of energy and enters an excited state. The donor fluorophore transfers its energy to an acceptor fluorophore when the two fluorophores are in close proximity by a process of non-radiative energy transfer. The acceptor fluorophore enters an excited state and eliminates the energy via radiative or non-radiative processes. Transfer of energy from the donor fluorophore to acceptor fluorophore only occurs if the two fluorophores are in close proximity.

Homogeneous Time Resolved Fluorescence (HTRF)

Homogeneous time resolved fluorescence (HTRF) uses FRET between two fluorophores and measures the fluorescent signals from a homogenous assay in which all components of the assay are present during measurement. The fluorescent signal from HTRF is measured after a time delay, thereby eliminating interfering signals. One example of the donor and acceptor fluorophores in HTRF include europium cryptate [(Eu)K] and XL665, respectively.

Luminescent Oxygen Channeling Assay (LOCI)

In the luminescent oxygen channeling assay (LOCI), the proximity detection pairs includes a first member which is a sensitizer particle that contains phthalocyanine. The phthalocyanine absorbs energy at 680 nm and produces singlet oxygen. The second member is a chemiluminescer particle that contains olefin which reacts with the singlet oxygen to produce chemiluminescence which decays in one second and is measured at 570 nm. The reaction with the singlet oxygen and the subsequent emission depends on the proximity of the first and second members of the proximity detection pair.

Transgenic Animals

The methods herein described can include providing a transgenic animal having a transgene which includes a nucleic acid which encodes a reporter molecule functionally linked to the control region of a gene. A number of methods can be used to obtain transgenic, non-human animals. A transgenic non-human animal refers to an animal that has gained an additional gene or portion thereof through the introduction of an exogenous nucleic acid sequence, i.e., transgene, into its own cells (e.g., both the somatic and germ cells), or into an ancestor's germ line.

There are a number of methods to introduce the exogenous DNA into the germ line (e.g., introduction into the germ or somatic cells) of an animal. One method is by microinjection of a the gene construct into the pronucleus of an early stage embryo, e.g., before the four-cell stage (Wagner et al. (1981) *Proc Natl Acad Sci USA* 78:5016; Brinster et al. (1985) *Proc Natl Acad Sci USA* 82:4438). The detailed procedure to produce such transgenic mice has been described (see e.g., Hogan, et al., Manipulating the Mouse Embryo, Cold Spring Harbour Laboratory, Cold Spring Harbour, N.Y. (1986); U.S. Pat. No. 5,175,383 (1992)). This procedure has also been adapted for other mammalian species (e.g., Hammer, et al. (1985) *Nature* 315:680; Murray, et al. (1989) *Reprod Fert Devl* 1:147; Pursel et al. (1987) *Vet Immunol Histopath* 17:303; Rexroad et al. (1990) *J Reprod Fert* 41 (suppl):119; Rexroad et al. (1989) *Molec Reprod Devl* 1:164; Simons et al.(1988) *BioTechnology* 6:179; Vize et al.(1988) *J Cell Sci* 90:295; and Wagner (1989) *Cell Biochem* 13B (suppl):164.

Another method for producing germ-line transgenic mammnals is through the use of embryonic stem cells. The gene construct may be introduced into embryonic stem cells by homologous recombination (Thomas et al. (1987) *Cell* 51:503; Capecchi (1989) *Science* 244:1288; Joyner et al. (1989) *Nature* 338:153). A suitable construct may also be introduced into the embryonic stem cells by DNA-mediated transfection, such as electroporation (Ausubel et al., Current Protocols in Molecular Biology, John Wiley & Sons (1987)). Detailed procedures for culturing embryonic stem cells (e.g. ESD-3, ATCC# CCL-1934, ES-E14TG-2a, ATCC# CCL-1821, American Type Culture Collection, Rockville, Md.)

and the methods of making transgenic mammals from embryonic stem cells can be found in Teratocarcinomas and Embryonic Stem Cells, A Practical Approach, ed. E. J. Robertson (IRL Press, 1987).

In the above methods for the generation of a germ-line transgenic mammals, the construct may be introduced as a linear construct, as a circular plasmid, or as a vector which may be incorporated and inherited as a transgene integrated into the host genome. The transgene may also be constructed so as to permit it to be inherited as an extrachromosomal plasmid (Gassmann et al. (1995) *Proc. Natl. Acad. Sci. USA* 92:1292).

The use of the array in an ex-vivo or in vivo assay, as disclosed herein, minimizes the number of animals or tissues needed to assay a plurality of treatments, and allows for the use of one or more of the plurality of addresses for performing precise internal controls.

A number of embodiments of the invention have been described. Nevertheless, it will be understood that various modifications may be made without departing from the spirit and scope of the invention. Accordingly, other embodiments are within the scope of the following claims.

What is claimed is:

1. A method of evaluating the effect of a plurality of test compounds on the signals produced by a reporter molecule of a tissue of a transgenic non-human animal, the method comprising:

providing a transgenic non-human animal whose genome comprises a transgene comprising a nucleic acid which encodes a reporter molecule functionally linked to the control region of a gene, the reporter molecule being the source of signals;

contacting a tissue from the transgenic animal with the plurality of test compounds to thereby form on the tissue an array of a plurality of individually addressable regions or addresses, each region or address of the plurality including a test compound which differs from those at other addresses of the plurality; and evaluating the signals produced by the reporter molecule at each of the plurality of regions or addresses thereby evaluating the effect of a plurality of test compounds on the signals produced by the reporter molecule in the tissue of the non-human transgenic animal.

2. The method of claim 1, wherein the tissue is skin.

3. The method of claim 1, wherein each test compound of the plurality is injected into the tissue.

4. The method of claim 1, wherein the signals are evaluated by scanning the tissue for the presence or absence of light of a predetermined wavelength.

5. The method of claim 1, wherein the array includes at least 4 addresses.

6. The method of claim 5, wherein the array includes at least 64 addresses.

7. The method of claim 1, wherein the addresses are present at a density of at least one address/cm$^2$.

8. The method of claim 7, wherein the addresses are present at a density of at least 50 address/cm$^2$.

9. The method of claim 1, wherein the reporter molecule is a green fluorescent protein.

10. The method of claim 1, wherein the tissue is in vivo.

11. The method of claim 1, wherein the tissue is ex vivo.

12. The method of claim 1, wherein the transgenic animal is a transgenic mouse.

13. The method of claim 12, wherein the mouse is a hairless mouse.

14. The method of claim 1, wherein the tissue is a tissue other than skin.

15. The method of claim 1, wherein the plurality of test compounds comprises one or more of environmental contaminants, toxic compounds, cosmetic compounds, and therapeutic compounds.

* * * * *